US012297216B2

(12) United States Patent
Kung et al.

(10) Patent No.: US 12,297,216 B2
(45) Date of Patent: May 13, 2025

(54) INORGANIC APPROACH TO RENDERING METAL-ORGANIC FRAMEWORKS ELECTRICALLY CONDUCTIVE

(71) Applicant: Northwestern University, Evanston, IL (US)

(72) Inventors: Chung-Wei Kung, Evanston, IL (US); Timothy Chiaan Wang, Pleasonton, CA (US); Joseph T. Hupp, Northfield, IL (US)

(73) Assignee: Northwestern University, Evanston, IL (US)

( * ) Notice: Subject to any disclaimer, the term of this patent is extended or adjusted under 35 U.S.C. 154(b) by 1112 days.

(21) Appl. No.: 17/260,101

(22) PCT Filed: Jul. 18, 2019

(86) PCT No.: PCT/US2019/042366
§ 371 (c)(1),
(2) Date: Jan. 13, 2021

(87) PCT Pub. No.: WO2020/018767
PCT Pub. Date: Jan. 23, 2020

(65) Prior Publication Data
US 2021/0269461 A1  Sep. 2, 2021

Related U.S. Application Data

(60) Provisional application No. 62/701,131, filed on Jul. 20, 2018.

(51) Int. Cl.
| | |
|---|---|
| *C07F 7/00* | (2006.01) |
| *B01J 20/28* | (2006.01) |
| *B01J 31/16* | (2006.01) |
| *C01B 37/00* | (2006.01) |
| *C07F 7/22* | (2006.01) |
| *G01N 27/04* | (2006.01) |
| *G01N 33/00* | (2006.01) |

(52) U.S. Cl.
CPC .......... *C07F 7/00* (2013.01); *B01J 20/28011* (2013.01); *B01J 20/28057* (2013.01); *B01J 20/28071* (2013.01); *B01J 20/28083* (2013.01); *B01J 31/1691* (2013.01); *C01B 37/00* (2013.01); *G01N 27/04* (2013.01); *G01N 33/005* (2013.01); *B01J 2531/48* (2013.01)

(58) Field of Classification Search
CPC ... C07F 7/00; C07F 7/22; C07F 7/2224; B01J 31/1691; B01J 2531/48
See application file for complete search history.

(56) References Cited

U.S. PATENT DOCUMENTS

| | | |
|---|---|---|
| 7,481,866 B2 | 1/2009 | Macgillivray et al. |
| 8,715,395 B2 | 5/2014 | Omary |
| 9,562,005 B2 | 2/2017 | Bury et al. |
| 9,610,560 B2 | 4/2017 | Farha et al. |
| 9,724,668 B2 | 8/2017 | Zhou et al. |
| 2006/0252641 A1 | 11/2006 | Yahgi et al. |
| 2011/0046335 A1 | 2/2011 | Fernandes |
| 2011/0297558 A1 | 12/2011 | Hill |
| 2012/0297982 A1 | 11/2012 | Dinca et al. |
| 2013/0139686 A1 | 6/2013 | Wilmer |
| 2013/0296162 A1 | 11/2013 | Wright |
| 2015/0031908 A1 | 1/2015 | Bury |
| 2015/0217268 A1 | 8/2015 | Farha et al. |
| 2017/0362167 A1 | 12/2017 | Farha et al. |
| 2018/0274013 A1 | 9/2018 | Zhang et al. |

FOREIGN PATENT DOCUMENTS

| | | |
|---|---|---|
| EP | 2578593 | 4/2013 |
| WO | WO 2016081685 A1 | 5/2016 |
| WO | WO 2019/173571 A1 | 9/2019 |

OTHER PUBLICATIONS

Q. Xia et al., 15 Nano Micro Small, 1-25 (Year: 2019).*
M. Van Vleet, 118 Chemical Reviews, 3681-3721 (2018) (Year: 2018).*
M. Ahamad et al., 49 Dalton Transactions, 14690-14705 (2020) (Year: 2020).*
Z. Yin et al., 378 Coordination Chemistry Reviews, 500-512 (2019) (Year: 2019).*
J. C. Slater, John C. 41 The Journal of Chemical Physics 3199-3204 (1964) (Year: 1964).*
C. Kung et al., 10 ACS Applied Materials & Interfaces, 30532-30540 (Aug. 16, 2018) (Year: 2018).*
J. Liu et al., 46 Chem. Soc. Rev., 5730-5770 (2017) (Year: 2017).*
S. Yuan, et al. 54 Angewandte Chemie International Edition 14696-14700 (2015) (Year: 2015).*
K. I. Otake, et al. 140 Journal of the American Chemical Society 8652-8656 (2018) (Year: 2018).*
T. Wang et al., 11 Nature Protocols, 149-162 (2016) (Year: 2016).*
Dhara et al., The Journal of Physical Chemistry Letters, 2945-2950 (2016) (Year: 2016).*
J. Mondloch, et al., 135 Journal of the American Chemical Society 10294-10297 (2013) (Year: 2013).*
Enshoroud-Oxford English Dictonary 2015 (Year: 2015).*

(Continued)

*Primary Examiner* — Alexander R Pagano
*Assistant Examiner* — Frank S. Hou
(74) *Attorney, Agent, or Firm* — Bell & Manning, LLC

(57) ABSTRACT

Electrically conductive, metal-organic framework (MOF) materials, methods of making the materials, and chemical sensors incorporating the materials are provided. The electrically conductive MOF materials are formed from mesoporous MOF crystals having continuous strands of electrically conductive inorganic oxides within their porous structures. The inorganic strands are formed by the condensed-phase grafting of molecular metal species onto MOF nodes.

8 Claims, 11 Drawing Sheets

(56) References Cited

OTHER PUBLICATIONS

P. Li, et al. "Hierarchically engineered mesoporous metal-organic frameworks toward cell-free immobilized enzyme systems." Chem 4.5 (2018): 1022-1034. (Year: 2018).*

Joseph E. Mondloch et al., "Vapor-Phase Metalation by Atomic Layer Deposition in a Metal-Organic Framework," J. Am. Chem. Soc. 2013, vol. 135; pp. 10294-10297.

Imad H. Kadhim et al., "Hydrogen Gas Sensor Based on Nanocrystalline SnO2 Thin Film Grown on Bare Si Substrates," Nan-Micro Lett., Published online: Aug. 19, 2015 by Springer; pp. 1-9.

Joseph E. Mondloch et al., "Destruction of chemical warfare agents using metal-organic frameworks," Nature Materials, Published online: Mar. 16, 2015; pp. 1-5.

Zhanyong Li et al., "Metal-Organic Framework Supported Cobalt Catalysts for the Oxidative Dehydrogenation of Propane at Low Temperatures," ACS Cent. Sci. 2017, vol. 3; pp. 31-38.

Kung, Chung-Wei, et al. "Inorganic "conductive glass" approach to rendering mesoporous metal-organic frameworks electronically conductive and chemically responsive." ACS applied materials & interfaces 10.36 (2018): 30532-30540.

Islamoglu, I.; Goswami, S.; Li, Z.; Howarth, A. J.; Farna, O. K.; Hupp, J. T., "Postsynthetic Tuning of Metal—Organic Frameworks for Targeted Applications," Acc. Chem. Res. 2017, 50 (4), 805-813.

Peters, A. W.; Li, Z.; Farha, O. K.; Hupp, J. T., "Toward Inexpensive Photocatalytic Hydrogen Evolution: A Nickel Sulfide Catalyst Supported on a High-Stability Metal—Organic Framework," ACS Appl. Mater. Interfaces 2016, 8 (32), 20675-20681.

Ahn, S.; Thornburg, N. E.; Li, Z.; Wang, T. C.; Gallington, L. C.; Chapman, K. W.; Notestein, J. M.; Hupp, J. T.; Farha, O. K., "Stable Metal—Organic Framework-Supported Niobium Catalysts," Inorg. Chem. 2016, 55 (22), 11954-11961.

Noh, H.; Cui, Y.; Peters, A. W.; Pahls, D. R.; Ortuño, M. A.; Vermeulen, N. A.; Cramer, C. J.; Gagliardi, L.; Hupp, J. T.; Farha, O. K., "An Exceptionally Stable Metal—Organic Framework Supported Molybdenum(Vi) Oxide Catalyst for Cyclohexene Epoxidation," J. Am. Chem. Soc. 2016, 138 (44), 14720-14726.

Li, Z.; Peters, A. W.; Platero-Prats, A. E.; Liu, J.; Kung, C.-W.; Noh, H.; DeStefano, M. R.; Schweitzer, N. M.; Chapman, K. W.; Hupp, J. T.; Farha, O. K., "Fine-Tuning the Activity of Metal—Organic Framework-Supported Cobalt Catalysts for the Oxidative Dehydrogenation of Propane," J. Am. Chem. Soc. 2017, 139 (42), 15251-15258.

The International Search Report and Written Opinion issued on Sep. 26, 2019 for International Patent Application No. PCT/US2019/042366; pp. 1-6.

Yaghi et al., Reticular synthesis and the design of new materials, Nature, vol. 423, Jun. 12, 2003, pp. 705-714.

G. Férey, Hybrid porous solids: past, present, future, Chemical Society Reviews, vol. 37, Sep. 19, 2007, pp. 191-214.

Horike et al., Soft porous crystals, Nature Chemistry, vol. 1, Nov. 23, 2009, pp. 695-704.

Lee et al., Metal-organic framework materials as catalysts, Chemical Society Reviews, vol. 38, Mar. 17, 2009, pp. 1450-1459.

Dinca et al., Hydrogen Storage in Microporous Metal-Organic Frameworks with Exposed Metal Sites, Angewandte Chemie Int. Ed., vol. 47, Aug. 8, 2008, pp. 6766-6779.

Bae et al., High Propene/Propane Selectivity in Isostructural Metal-Organic Frameworks with High Densities of Open Metal Sites, Angewandte Chemie Int. Ed., vol. 51, Jan. 16, 2012, pp. 1857-1860.

S. Cohen, Postsynthetic Methods for the Functionalization of Metal-Organic Frameworks, Chemical Reviews, vol. 112, Sep. 14, 2011, pp. 970-1000.

Sumida et al., Impact of Metal and Anion Substitutions on the Hydrogen Storage Properties of M-BTT Metal-Organic Frameworks, Journal of the American Chemical Society, vol. 135, Dec. 17, 2012, pp. 1083-1091.

Meilikhov et al., Metals@MOFs—Loading MOFs with Metal Nanoparticles for Hybrid Functions, European Journal of Inorganic Chemistry, vol. 2010, No. 24, Jul. 9, 2010, pp. 3701-3714.

S. George, Atomic Layer Deposition: An Overview, Chemical Reviews, vol. 110, No. 1, Nov. 30, 2009, pp. 111-131.

R. Puurunen, Surface chemistry of atomic layer deposition: A case study for the trimethylaluminum/water process, Journal of Applied Physics, vol. 97, No. 121301, Jun. 30, 2005, pp. 1-52.

Marichy et al., Atomic Layer Deposition of Nanostructured Materials for Energy and Environmental Applications, Advanced Materials, vol. 24, Jan. 26, 2012, pp. 1017-1032.

J. Elam, Chapter 10, Coatings on High Aspect Ratio Structures, Atomic Layer Deposition of Nanostructured Materials, First Edition, Edited by Nicola Pinna and Mato Knez, Published 2012 by Wiley-VCH Verlag Gmbh & Co. KGaA, Jan. 2, 2012, pp. 227-249.

Lu et al., Coking- and Sintering-Resistant Palladium Catalysts Achieved Through Atomic Layer Deposition, Science, vol. 335, Mar. 9, 2012, pp. 1205-1208.

Liu et al., Robust, Functional Nanocrystal Solids by Infilling with Atomic Layer Deposition, Nano Letters, vol. 11, Oct. 24, 2011, pp. 5349-5355.

Hamann et al., Aerogel Templated ZnO Dye-Sensitized Solar Cells, Advanced Materials, vol. 20, Apr. 9, 2008, pp. 1560-1564.

Cavka et al., A New Zirconium Inorganic Building Brick Forming Metal Organic Frameworks with Exceptional Stability, Journal of the American Chemical Society, vol. 130, Sep. 26, 2008, pp. 13850-13851.

Morris et al., Synthesis, Structure, and Metalation of Two New Highly Porous Zirconium Metal-Organic Frameworks, Inorganic Chemistry, vol. 51, Jun. 7, 2012, pp. 6443-6445.

Feng et al., Zirconium-Metalloporphyrin PCN-222: Mesoporous Metal-Organic Frameworks with Ultrahigh Stability as Biomimetic Catalysts, Angewandte Chemie Int. Ed., vol. 51, Aug. 21, 2012, pp. 10307-10310.

Bon et al., Zr- and Hf-Based Metal-Organic Frameworks: Tracking Down the Polymorphism, Crystal Growth & Design, vol. 13, No. 3, Feb. 14, 2013, pp. 1231-1237.

Gordon et al., A Kinetic Model for Step Coverage by Atomic Layer Deposition in Narrow Holes or Trenches, Chemical Vapor Deposition, vol. 9, No. 2, 2003, pp. 73-78.

Elam et al., Conformal Coating on Ultrahigh-Aspect-Ratio Nanopores of Anodic Alumina by Atomic Layer Deposition, Chemistry of Materials, vol. 15, No. 18, Aug. 14, 2003, pp. 3507-3517.

Valenzano et al., Disclosing the Complex Structure of UiO-66 Metal Organic Framework: A Synergic Combination of Experiment and Theory, Chemistry of Materials, vol. 23, Mar. 4, 2011, pp. 1700-1718.

Larabi et al., Titration of $Zr_3(\mu\text{-OH})$ Hydroxy Groups at the Cornerstones of Bulk MOF UiO-67, $[Zr_6O_4(OH)_4(\text{biphenyldicarboxylate})_6]$, and Their Reaction with $[AuMe(PMe_3)]$, European Journal of Inorganic Chemistry, vol. 2012, No. 18, May 11, 2012, pp. 3014-3022.

He et al., Intrared Studies of the Adsorption of Synthesis Gas on Zirconium Dioxide, Journal of Catalysis, vol. 87, 1984, pp. 381-388.

Cui et al., Stereoselective construction of fluorinated indanone derivatives via a triple cascade Lewis acid-catalyzed reaction, Chemical Communications, vol. 2007, No. 22, Apr. 4, 2007, pp. 2284-2286.

Burnett et al., Stepwise Synthesis of Metal-Organic Frameworks: Replacement of Structural Organic Linkers, J. Am. Chem. Soc., vol. 133, Jun. 15, 2011, pp. 9984-9987.

Bury et al., Control over Catenation in Pillared Paddlewheel Metal-Organic Framework Materials via Solvent-Assisted Linker Exchange, Chem. Mater., vol. 25, Feb. 9, 2013, pp. 739-744.

Dalvi et al., Understanding the Effectiveness of Fluorocarbon Ligands in Dispersing Nanoparticles in Supercritical Carbon Dioxide, J. Phys. Chem. C, vol. 114, Aug. 31, 2010, pp. 15553-15561.

Deria et al., Perfluoroalkane Functionalization of NU-1000 via Solvent-Assisted Ligand Incorporation: Synthesis and CO2 Adsorption Studies, J. Am. Chem. Soc., vol. 135, Oct. 31, 2013, pp. 16801-16804.

DeSimone et al., Dispersion Polymerizations in Supercritical Carbon Dioxide, Science, vol. 265, Jul. 15, 1994, pp. 356-359.

(56) References Cited

OTHER PUBLICATIONS

Farha et al., An Example of Node-Based Postassembly Elaboration of a Hydrogen-Sorbing, Metal-Organic Framework Material, Inorg. Chem., vol. 47, Oct. 18, 2008, pp. 10223-10225.

Fernandez et al., Gas-Induced Expansion and Contraction of a Fluorinated Metal-Organic Framework, Crystal Growth & Design, vol. 10, No. 3, Jan. 29, 2010, pp. 1037-1039.

Fried et al., The molecular basis of $CO_2$ interaction with polymers containing fluorinated groups: computational chemistry of model compounds and molecular simulation of poly[bis(2,2,2-trifluoroethoxy)phosphazene], Polymer, vol. 44, 2003, pp. 4363-4372.

Hwang et al., Amine Grafting on Coordinatively Unsaturated Metal Centers of MOFs: Consequences for Catalysis and Metal Encapsulation, Angew. Chem. Int. Ed., vol. 47, Apr. 24, 2008, pp. 4144-4148.

Seo et al., A homochiral metal-organic porous material for enantioselective separation and catalysis, Nature, vol. 404, Apr. 27, 2000, pp. 982-986.

Kanoo et al., Unusual room temperature $CO_2$ uptake in a fluoro-functionalized MOF: insight from Raman spectroscopy and theoretical studies, Chem. Commun., vol. 48, Jun. 29, 2012, pp. 8487-8489.

Karagiaridi et al., Opening ZIF-8: A Catalytically Active Zeolitic Imidazolate Framework of Sodalite Topology with Unsubstituted Linkers, J. Am. Chem. Soc., vol. 134, Oct. 22, 2012, pp. 18790-18796.

Karagiaridi et al., Synthesis and characterization of isostructural cadmium zeolitic imidazolate frameworks via solvent-assisted linker exchange, Chem. Sci., vol. 3, Aug. 7, 2012, pp. 3256-3260.

Kiang et al., Variable Pore Size, Variable Chemical Functionality, and an Example of Reactivity within Porous Phenylacetylene Silver Salts, J. Am. Chem. Soc., vol. 121, Aug. 25, 1999, pp. 8204-8215.

Kim et al., Postsynthetic ligand exchange as a route to functionalization of 'inert' metal-organic frameworks, Chem. Sci., vol. 3, Sep. 13, 2011, pp. 126-130.

Li et al., Stepwise Ligand Exchange for the Preparation of a Family of Mesoporous MOFs, J. Am. Chem. Soc., vol. 135, May 20, 2013, pp. 11688-11691.

Noro et al., Highly Selective $CO_2$ Adsorption Accompanied with Low-Energy Regeneration in a Two-Dimensional Cu(II) Porous Coordination Polymer with Inorganic Fluorinated $PF_6$—Anions, Inorg. Chem., vol. 52, Dec. 18, 2012, pp. 280-285.

Nugent et al., Porous materials with optimal adsorption thermodynamics and kinetics for $CO_2$ separation, Nature, vol. 495, Feb. 27, 2013, pp. 80-84.

Takaishi et al., Solvent-assisted linker exchange (SALE) and post-assembly metallation in porphyrinic metal-organic framework materials, Chem. Sci., vol. 4, Dec. 7, 2012, pp. 1509-1513.

Wilmer et al., Structure-property relationships of porous materials for carbon dioxide separation and capture, Energy Environ. Sci., vol. 5, Sep. 21, 2012, pp. 9849-9856.

Xue et al., Tunable Rare-Earth fcu-MOFs: A Platform for Systematic Enhancement of $CO_2$ Adsorption Energetics and Uptake, J. Am. Chem. Soc., vol. 135, Apr. 22, 2013, pp. 7660-7667.

Yang et al., Fluorous Metal-Organic Frameworks with Superior Adsorption and Hydrophobic Properties toward Oil Spill Cleanup and Hydrocarbon Storage, J. Am. Chem. Soc., vol. 133, Oct. 7, 2011, pp. 18094-18097.

Deria, P., et al., "Versatile functionalization of the NU-1000 platform by solvent-assisted ligand incorporation," *Chemical Communications*, Jan. 9, 2014, vol. 50, No. 16, 4 pp.

International Search Report and Written Opinion for Intl. Patent Appl. No. PCT/2015/014082, mailed on May 29, 2015, 11 pp.

International Search Report and Written Opinion mailed in PCT/US15/61475, Mar. 4, 2016.

Beyzavi et al., A hafnium-based metal organic framework as an efficient and multifunctional catalyst for facile $CO_2$ fixation and regioselective and enantioretentive epoxide activation, Journal of the American Chemical Society, vol. 136, No. 45, Oct. 30, 2014, pp. 15861-15864.

Stephenson et al., Research update: A hafnium-based metalorganic framework as a catalyst for regioselective ring-opening of epoxides with a mild hydride source, APL Materials, vol. 2, No. 12, article No. 123901, Oct. 27, 2014, pp. 1-5.

Furukawa et al., The chemistry and applications of metal-organic frameworks, Science, vol. 341, article No. 1230444, Aug. 30, 2013.

\* cited by examiner

INORGANIC APPROACH TO RENDERING METAL-ORGANIC FRAMEWORKS ELECTRICALLY CONDUCTIVE

CROSS-REFERENCE TO RELATED APPLICATIONS

This application is a National Stage of International Application No. PCT/US19/42366, filed Jul. 18, 2019, which claims the benefit of U.S. Patent Application No. 62/701,131, filed Jul. 20, 2018, the contents of which are herein incorporated by reference.

REFERENCE TO GOVERNMENT RIGHTS

This invention was made with government support under DE-SC0001059 awarded by the U.S. Department of Energy. The government has certain rights in the invention.

BACKGROUND

Metal-organic frameworks (MOFs) constitute an enormous and growing class of porous (or potentially porous) crystalline materials. By choosing suitable component organic linkers and inorganic nodes, MOFs with desirable pore composition, periodic chemical functionality, ultrahigh specific surface area, and other properties can be obtained. Further, they can be obtained in great variety—both in silico and in real space. The periodic intra-framework functionality of MOFs allows for the high-density installation of well-defined, yet well-separated active species with frameworks functioning as porous supports.

Central to the potential application of MOFs specifically to electrochemical, molecular electronic, or resistive chemical sensing problems is electrical conductivity. Most MOFs, however, are effectively insulating at low bias. Indeed, only a few tens of MOFs have thus far been shown to display appreciable electrical conductivity. Among the experimentally demonstrated routes to engendering electrical conductivity, while retaining molecular-scale porosity, are as follows: formation of π-stacked pathways, formation of two-dimensional MOFs featuring extended π-conjugation, formation of continuous arrays of electron-donor/electron-acceptor complexes (charge-transfer complexes) between MOF hosts and molecular guests, use of sulfur-based ligands to facilitate energy-level matching and charge delocalization into open-shell, node-sited metal ions, and polymerization of tethered oligomers or, at low loading, adsorbed monomers, within MOF pores to yield MOF/conducting-polymer composites. Yet another approach is linker-to-linker hopping at the redox potentials of selected organic linkers (or molecule-to-molecule hopping at the redox potentials of species installed in the pores of MOFs) under electrochemical conditions.

What the above approaches have in common is a reliance upon organic species/components to sustain, or help sustain, charge transport. To the extent that these species possess radical character, diminished chemical stability and eventual loss of conductivity may be anticipated.

SUMMARY

MOF materials, methods of making the materials, and chemical sensors incorporating the materials are provided.

One embodiment of a metal-organic framework material includes: a porous metal-organic framework comprising inorganic nodes connected by organic linkers; and a plurality of continuous strands comprising an inorganic oxide running through the metal-organic framework. The metal-organic framework material is porous.

One embodiment of a method of forming a metal-organic framework material starts with a porous metal-organic framework that includes inorganic nodes connected by organic linkers, wherein the inorganic nodes are capped by hydroxo ligands, aquo ligands, oxo ligands, or a combination thereof. The method includes the steps of: (a) reacting the hydroxo ligands, aquo ligands, and/or oxo ligands on the inorganic nodes with organometallic complexes in a liquid solution to graft the organometallic complexes onto the inorganic nodes, the organometallic complexes comprising a metal ion bound to one or more organic ligands; (b) exposing the organometallic complexes grafted to the inorganic nodes to steam to replace the organic ligands in the organometallic complexes with secondary hydroxo ligands, aquo ligands, oxo ligands, or a combination thereof to provide metal oxide species grafted to the inorganic nodes; (c) reacting the secondary hydroxo ligands, aquo ligands, oxo ligands, or combination thereof with organometallic complexes in a liquid solution to graft the organometallic complexes to the metal oxide species; (d) exposing the organometallic complexes grafted to the metal oxide species to steam to replace the organic ligands in the organometallic complexes with secondary hydroxo ligands, aquo ligands, oxo ligands, or a combination thereof, and (e) repeating steps (c) and (d) a sufficient number of times to form continuous metal oxide strands from the metal oxide species.

One embodiment of a method of detecting hydrogen uses a metal-organic framework material that includes: a porous metal-organic framework, the metal-organic framework comprising inorganic nodes connected by organic linkers; and continuous strands of an electrically conductive material comprising an inorganic oxide running through the metal-organic framework, wherein the metal-organic framework material is porous and electrically conductive. The method includes the steps of: exposing the metal-organic framework material to an environment comprising hydrogen; and measuring an increase in the conductance of the metal-organic framework material.

BRIEF DESCRIPTION OF THE DRAWINGS

Illustrative embodiments of the invention will hereafter be described with reference to the accompanying drawings.

DETAILED DESCRIPTION

MOF materials, methods of making the materials, and chemical sensors incorporating the materials are provided.

Some embodiments of the MOF materials are electrically conductive. The electrically conductive MOF materials are formed from mesoporous MOF crystals having continuous strands of electrically conductive inorganic oxides within their porous structures. Non-conductive MOF materials are formed from mesoporous MOF crystals having continuous strands of non-electrically conductive inorganic oxides within their porous structures. The inorganic strands are formed by the condensed-phase grafting of molecular metal species onto MOF nodes via reactions with hydroxyl, aqua ligands, and/or oxo ligands present at the nodes' surfaces. This self-limiting SIM process provides a robust inorganic approach that permits retention of the MOF's crystallinity and porosity.

MOFs are hybrid, crystalline, porous materials made from metal-ligand networks that include inorganic nodes connected by organic linkers. The inorganic nodes or vertices in the framework can be composed of metal ions or clusters. By convention, carboxylates (or other linker terminal groups or atoms) are often represented as components of the nodes. These nodes are connected by coordination bonds to organic linkers, which commonly contain carboxylate, phosphonate, pyridyl, and imidazolate or other azolate functional groups. In the zirconium MOFs, the nodes comprise zirconium atoms or zirconium clusters.

The SIM process can be carried out on MOFs having hydroxyl and/or aquo ligands present on their nodes. Examples of such MOFs include, but are not limited to, zirconium MOFs (i.e., MOFs having zirconium-based nodes), hafnium MOFs, cerium MOFs, and thorium MOFs. Notable characteristics of zirconium MOFs include high thermal, mechanical, and chemical stability (e.g., stability toward $H_2S$, ammonia, steam, aqueous acid, and/or hydrogen peroxide), as well as the ability to present well-defined, node-based grafting sites for chemical and structural elaboration and, thus, for introduction of specific functional properties.

The MOFs include channel-type MOFs that present a hierarchical pore structure comprising a first set of large hexagonal channels and a second set of smaller triangular channels, running alongside of the large hexagonal channels. The hexagonal channels impart the MOFs with mesoporosity and typically have channel diameters in the range from about 20 Å to about 70 Å.

By way of illustration, MOFs having a framework with a csq-net topology characterized by large hexagonal channels and smaller triangular channels may be used to immobilize various enzymes. MOFs of this type are described in Mondloch et al., *J. Am. Chem. Soc.* 135, 10294-10297 (2013) and include the MOF designated NU-1000. NU-1000 has hexagonal channels with a diameter of 3.1 nm as well as triangular channels with an edge length of 1.5 nm, with windows connecting the two channels.

Figures 5A, 5B:
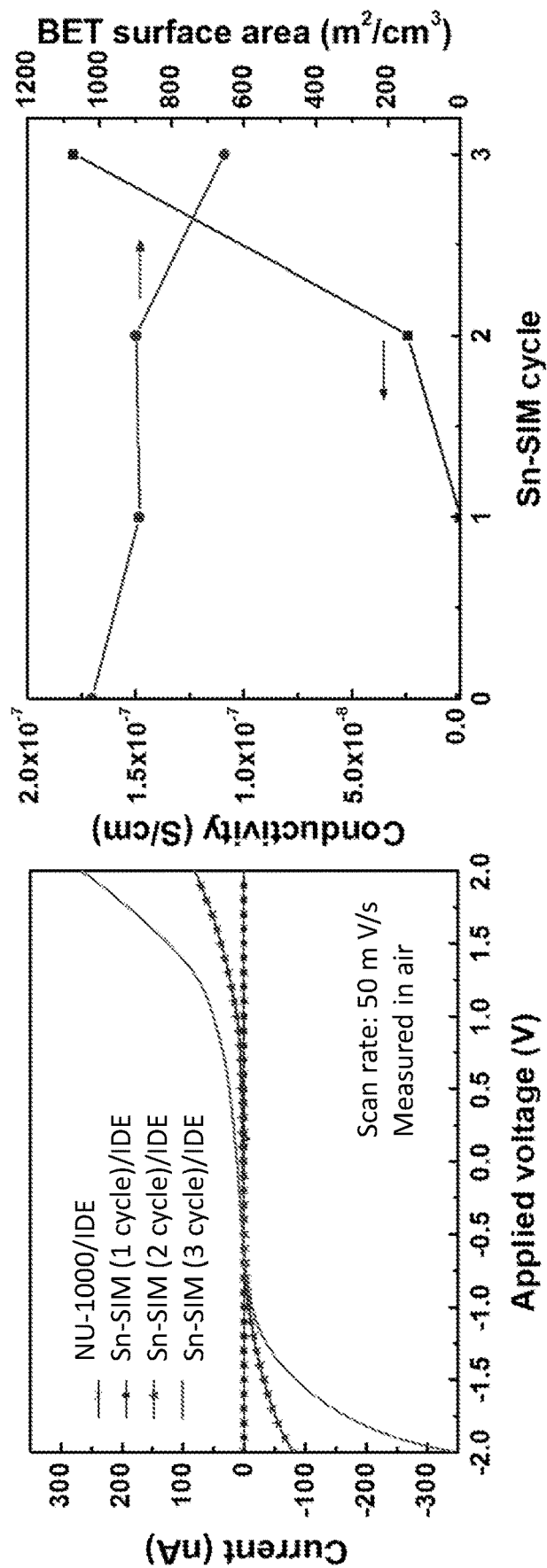
FIG. 5A depicts I-V curves of NU-1000/interdigitated electrode (IDE), Sn-SIM (1 cycle)/IDE, Sn-SIM (2 cycle)/IDE, and Sn-SIM (3 cycle)/IDE, measured in air at room temperature.
FIG. 5B shows electrical conductivity and Brunauer-Emmett-Teller (BET) surface area of NU-1000, Sn-SIM (1 cycle), Sn-SIM (2 cycle), and Sn-SIM (3 cycle).
Figure 6A:
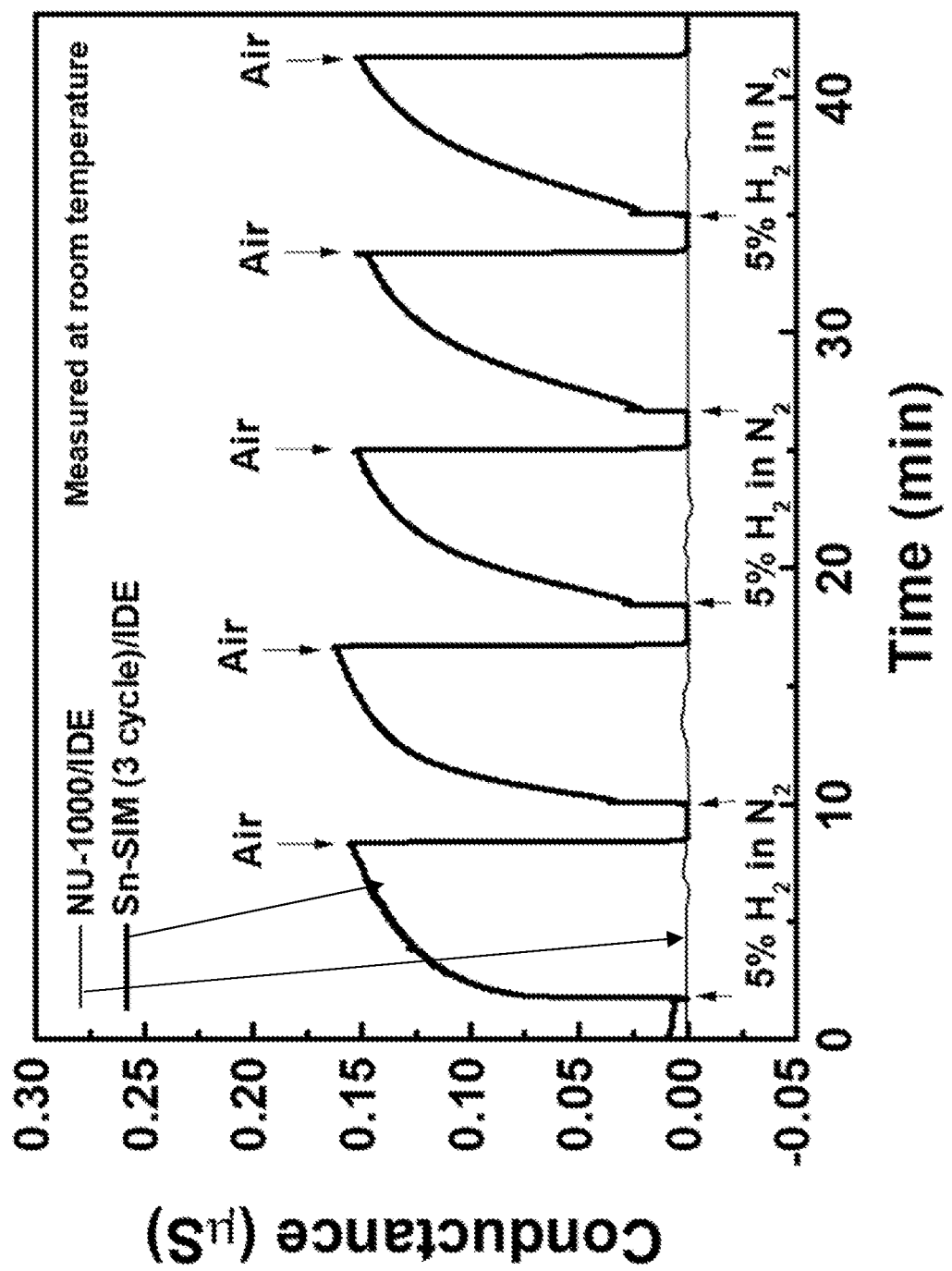
FIG. 6A depicts the change in conductance of the Sn-SIM (3 cycle)/IDE and NU-1000/IDE flowed with 5% $H_2$ in $N_2$ or air, measured at room temperature.
Figure 6B:
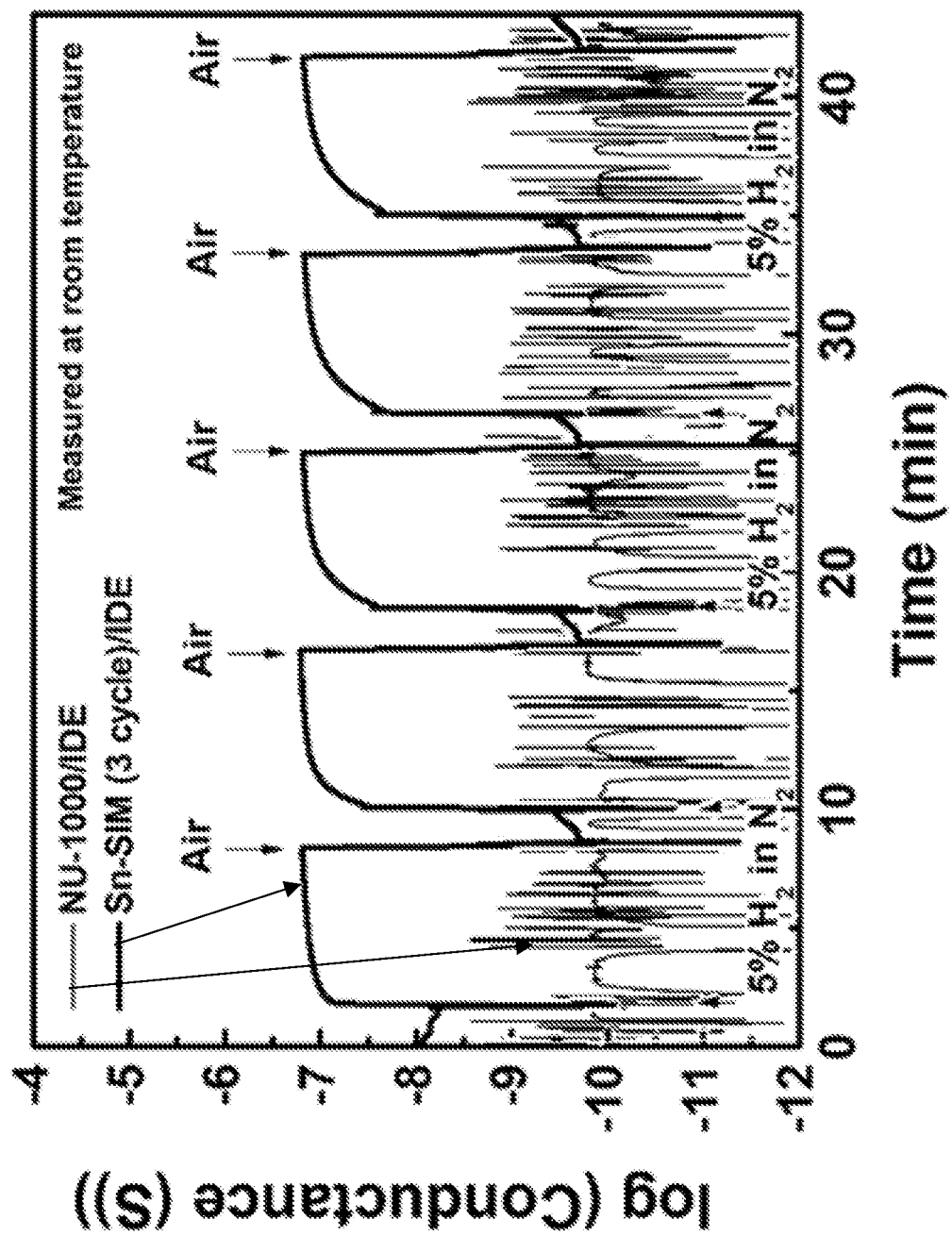
FIG. 6B depicts a plot of the data in FIG. 6A with the conductance presented in log scale.
Figure 7:
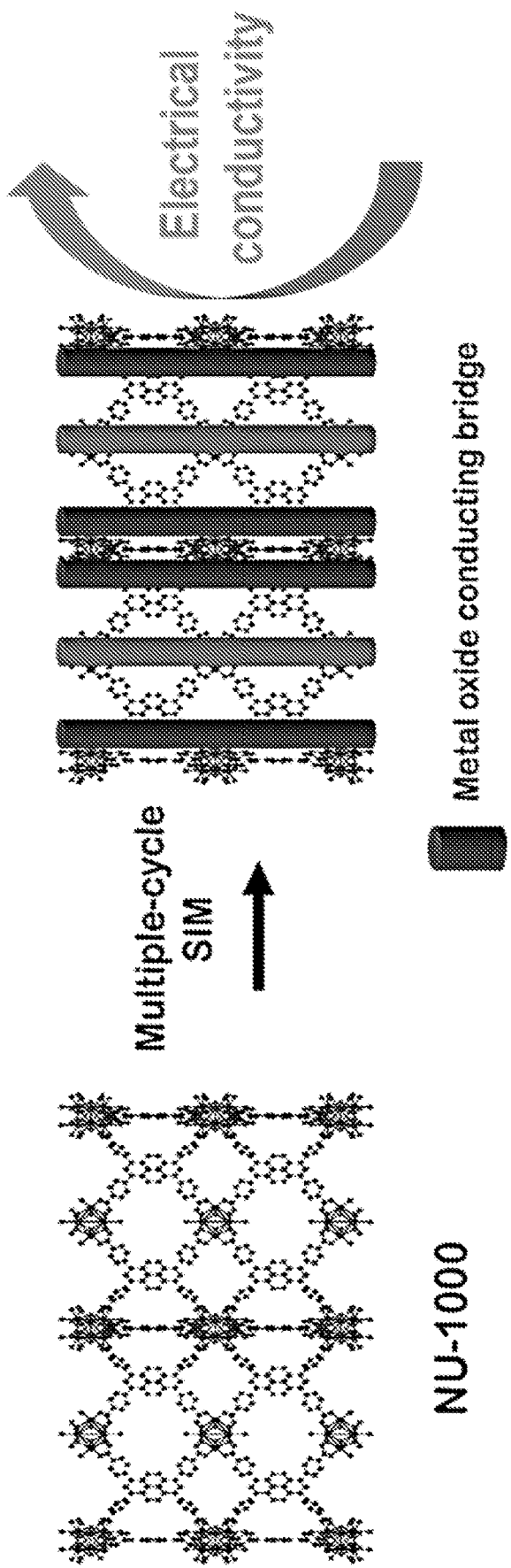
FIG. 7 illustrates the conversion of an electrically insulating MOF to an electrically conductive MOF.

The zirconium MOFs having a csq-net topology include mesoporous zirconium MOFs having eight $Zr_6$ cluster nodes connected by tetratropic linkers, where a $Zr_6$ cluster node has the structure $Zr_6(\mu_3\text{-}O)_4(\mu_3\text{-}OH)_4(OH)_4(H_2O)_4$ or a variation of that structure in which some or all of the hydroxo ligands are replaced with oxo and/or aquo ligands. For example, one family of such MOFs has pyrene-based tetratopic linkers connecting the metal cluster nodes. The pyrene-based linkers can include various aryl groups in their linker chains, including phenyl groups, bi-phenyl groups, and napthyl groups. The structure of these types of MOFs are illustrated in FIGS. 5A, 5B, 5C, 5D, and 5E of PCT application number WO/2017213871, which show MOFs designated NU-1006, NU-1005, NU-1004, NU-1003, and NU-1000, respectively. Other csq-net topology MOFs include those having eight $Zr_6$ cluster nodes connected by ethene-1,1,2,2-tetrayl)tetrakis-(([1,1'-biphenyl]-4-carboxylic acid))) (ETTC) linkers. The structure of the PCN-128 MOF is shown in FIG. 6 of PCT application number WO/2017213871 and described in Zhang et al., *J. Am. Chem. Soc.*, 2015, 137, 10064-10067. Still other csq-net topology MOFs have $Zr_6$ cluster nodes connected by parylene-based tetratopic linkers. The structure for one such MOF, UMCM-313, is shown in FIG. 7 of PCT application number WO/2017213871 and described in Ma et al., *Cryst. Growth Des.*, 2016, 16 (7), pp 4148-4153. MOFs having a csq-net topology formed from $Zr_6$ clusters connected by porphyrin-based linkers can also be used. FIG. 8 of PCT application number WO/2017213871 shows the structure on one such MOF, denoted PCN-222. Methods for making these MOFs are illustrated in PCT application number WO/2017213871, the disclosure of which in incorporated herein by reference.

Other suitable MOFs include MOFs that are isostructural with the Zr-based MOF, but are based on different transition metals, lanthanides, and actinides. These include isostructural Hf-, Ce-, and Th-based MOFs. Illustrative examples of hafnium-based MOFs are described in Hassan, et al. "A hafnium-based metal-organic framework as an efficient and multifunctional catalyst for facile $CO_2$ fixation and regioselective and enantioretentive epoxide activation." *Journal of the American Chemical Society* 136.45 (2014): 15861-15864 and in Ting, et al. "Fast and scalable synthesis of uniform zirconium-, hafnium-based metal-organic framework nanocrystals." *Nanoscale* 9.48 (2017): 19209-19215. Illustrative examples of cerium-based MOFs are described in Islamoglu, Timur, et al. "Cerium (IV) vs zirconium (IV) based metal-organic frameworks for detoxification of a nerve agent." *Chemistry of Materials* 29.7 (2017): 2672-2675 and in Dalapati, Rana, et al. "A cerium-based metal-organic framework having inherent oxidase-like activity applicable for colorimetric sensing of biothiols and aerobic oxidation of thiols." *CrystEngConn* 19.39 (2017): 5915-5925. Illustrative examples of thallium-based MOFs, zirconium-based MOFs, hafnium-based MOFs, and cerium-based MOFs are also described in Xingjie, et al. "Vanadium Catalyst on Isostructural Transition Metal, Lanthanide, and Actinide Based Metal-Organic Frameworks for Alcohol Oxidation." *Journal of the American Chemical Society* (2019).

The SIM process is carried out on MOFs that have hydroxo, aquo, and/or oxo ligands bound their nodes. One embodiment of a SIM process includes the step of reacting the hydroxo ligands, aquo ligands, and/or oxo ligands on their nodes with organometallic complexes in the condensed phase to graft the organometallic complexes onto the nodes. The organometallic complexes include a metal ion bound to one or more organic ligands. It is the metal ion of the organometallic complexes that will be converted into the inorganic oxide strands after multiple SIM cycles. The product of this initial reaction can then be removed from solution and, optionally dried. The organometallic complexes that are grafted to the MOF nodes are then exposed to steam to replace the organic ligands in the organometallic complexes with secondary hydroxo ligands, aquo ligands, oxo ligands, or a combination thereof. This provides metal-oxy clusters composed of hydroxo-, aquo-, and/or oxo-functionalized metal oxide species grafted to the nodes. For the purpose of this disclosure, such SIM-synthesized clusters will be referred to as metal oxides, although the metal ion-containing species ligate hydroxide, and possibly also water, in addition to $O^2$. The term "secondary" is used here to distinguish the hydroxo ligands, aquo ligands, oxo ligands that are initially present on the nodes of the MOF (primary hydroxo ligands, aquo ligands, and oxo ligands) from the hydroxo ligands, aquo ligands, oxo ligands that become bound to the grafted metal ions during the SIM process.

In subsequent cycles of the process, the newly formed secondary hydroxo ligands, aquo ligands, oxo ligands, or combination thereof are reacted with additional organometallic complexes in liquid solution to graft the organometallic complexes to the metal oxide species. The organometallic complexes in the subsequent cycles may be the same as or different from the organometallic complexes used in previous cycles. The resulting, newly grafted organometallic complexes are then exposed to steam to replace their organic ligands with a new set of secondary hydroxo ligands, aquo ligands, and/or oxo ligands. By introducing the new O—H presenting ligands on the modified-MOF nodes, the steam step serves to reset the material to reactive form, thus enabling a second self-limiting metal grafting step to be run. Thus, the cycle can be repeated one or more times until the metal ion loading on the nodes is sufficiently high to form continuous metal oxide strands that are electrically conductive.

For the synthesis of electrically conductive MOF materials, the metal ion of the organometallic complexes should be a metal having an electrically conductive oxide. Tin ions, including tin(IV) ions are examples of ions that can be used in the organometallic compounds for the formation of tin oxide strands. The tin oxide strands may comprise fluorine-doped tin oxide, indium-doped tin oxide, and/or may take the form of tin oxide nanowires. Doped metal oxide strands can be made by running a small number of SIM cycles using the selected dopant element, such as indium, among the multiple SIM cycles used to form the strands. The number of dopant SIM cycles used would depend on the desired level of doping. The synthesis of an electrically conductive NU-1000 MOF having continuous strands of oxy-tin(IV) oriented exclusively along its c-axis is illustrated in the Example. Other metal ions that can be used to form the electrically conductive metal oxide strands include indium and cerium. Metal ions that can be used to form non-electrically conductive MOFs include cobalt, nickel, and copper.

Various aspects of the inventions described herein are based, at least in part, on the inventors' discovery that continuous electrically conducting strands can be formed by enshrouding electrically insulating nodes in the MOFs with conductive oxides when the organometallic compound deposition is carried out from a condensed phase (i.e., for a liquid solution), rather than in vacuum. Without intending to be bound to any particular theory, it is believed that heat is released at a much slower rate during the reactions in the condensed phase relative to the heat release in a vacuum based deposition. This slower heat release prevents the reactive ligands from boiling off and allows the organometallic compounds to graft over the surface of the nodes to such an extent that a continuous electrically conductively pathway is created through the MOF. The continuous strands formed within the pores of the MOFs can be parallel, running along the same axis within the MOF.

The condensed-phase reactions between the organometallic complexes and the MOFs nodes in the initial SIM cycle and the secondary hydroxo, aquo, and/or oxo ligands in subsequent SIM cycles can be carried by dissolving the MOFs and the organometallic complexes in an organic solvent, such as heptane. Suitable organometallic compounds that can be used in the SIM synthesis include bis(N,N'-di-i-propylacetamidinato)tin(II). Other illustrative examples of organometallic compounds that can be used in the SIM synthesis include bis(N,N'-di-i-propylacetamidinato)cobalt, bis(N,N'-di-i-propylacetamidinato)nickel, and bis(dimethylamino-2-propoxy)copper. Guidance regarding the selection of other organometallic compounds can be found in the existing literature for atomic layer deposition of metal-containing materials.

The electrically conductive strands formed via SIM can be effectively one-dimensional, having widths of 5 nm or less, 2 nm or less, and 1 nm or less and can be oriented along a single axis of the MOF crystal, such as the c-axis. As a result, the electrical conductivity can be highly anisotropic—and this behavior can extend to thermal conductivity. In addition, because the electrically conductive MOFs retain their mesoporosity, they can be used in aqueous electrocatalysis and other applications where electrical conductivity and high internal surface areas are desirable. By way of illustration, the porosity of the electrically conductive MOFs is typically reduced by 50% or less relative to the MOF starting crystals, with channel diameters that are reduced by, for example, less than 20%.

Embodiments of the electrically conductive MOF materials can have electrical conductivities of $1 \times 10^{-6}$ S/cm or higher. This includes embodiments of the MOF materials that have electrical conductivities of $1 \times 10^{-7}$ S/cm or higher and $2 \times 10^{-7}$ S/cm or higher.

Embodiments of the electrically conductive MOF materials can have BET surface areas of 300 $m^2/g$ or higher. This includes embodiments of the MOF materials that have BET surface areas of 500 $m^2/g$ or higher.

Methods of measuring electrical conductance and BET surface area are described in the Example. Unless otherwise indicated, measured and measurable values recited herein refer to those values at room temperature (~25° C.) and atmospheric pressure.

Hydrogen sensing is an example of an application for the electrically conductive MOFs. Such sensors take advantage of the reversible $H_2$ doping of the inorganic oxide (e.g., metal oxide) strands in the MOFs. In a hydrogen sensor, an electrically conductive MOF of the type described herein, is exposed to an environment containing (or suspected of containing) hydrogen. As a result of this exposure, the metal oxide becomes reversibly doped and an increase in the conductance of the electrically conductive MOF material can be measured. The conductance increase can be measured directly or it can be measured indirectly by measuring a decrease in the material's resistance.

EXAMPLE

This Example illustrates an inorganic approach to engendering electrical conductivity within a representative mesoporous Zr-MOF, NU-1000. (See, e.g., Mondloch et al., 2013) Briefly, the multiple reactive aqua and hydroxo ligands of the eight-connected nodes of NU-1000 and the compound's mesoporosity (31 Å diameter hexagonal pores) were used to install tin(IV) ions via the SIM process and fabricate continuous, transparent strands of tin-oxide—essentially, conductive glass (cf, fluorine-doped (bulk) tin oxide, indium-doped (bulk) tin-oxide, arrays of tin-oxide nano-wires, etc.). The self-limiting nature of SIM chemistry was relied upon to avoid over-filling MOF channels and thereby eliminate the material's inherent mesoporosity. Indeed, MOF channel functionalization with conductive tin oxide is accompanied by a decrease of effective mesopore diameter of only a few angstroms (~31→27 Å). Finally, this Example shows how the engendered conductivity can be used to render the MOF functional as a rapidly responding, resistive sensor for hydrogen gas.

Experimental Section

Chemicals. All chemicals including N,N-dimethylformamide (DMF) (Fisher Chemical, ≥99.8%), benzoic acid (Sigma-Aldrich, ≥99.5%), zirconyl chloride octahydrate (Sigma-Aldrich, 98%), hydrochloric acid (HCl) (36.5-38.0%, Avantor), acetone (Fisher Chemical, ≥99.5%), bis(N,N'-di-i-propylacetamidinato)tin(II) ($Sn(amd)_2$) (Strem, 99%), and heptane (Sigma-Aldrich, anhydrous, 99%) were used as received. Deionized water was used for preparing aqueous solutions. The chemicals for synthesizing the 1,3,6,8-tetrakis(p-benzoic acid)pyrene ($H_4TBAPy$) linkers were all the same as those reported in a previous work. (See, e.g., Wang, T. C., et al., *Nat. Protocols* 2016, 11 (1), 149-162.)

Synthesis of tin oxide installed in NU-1000 (Sn-SIM). NU-1000 was synthesized according to the procedures reported in a previous study. (See, e.g., Wang, et al., 2016) Thereafter, 120 mg of $Sn(amd)_2$ was dissolved in 20 mL of anhydrous heptane in an argon-filled glove box, and 80 mg of NU-1000 was added in to the obtained solution. The mixture was kept for 24 h in the glove box at room temperature. The mixture was then decanted, and the powder was washed with 20 mL of heptane two times, waiting at least 6 h in between each washing step. Fresh heptane (20 mL) was then added, and the mixture was kept overnight. After the final decantation, the obtained sample was removed from the glove box and dried in an oven at 100° C. in air overnight to remove the residual heptane. Thereafter, equal or less than 50 mg of the obtained powder was packed in a custom-made stainless steel powder sample holder, and the holder was placed in an atomic layer deposition (ALD) chamber (Savanah S100 system, Ultratech Cambridge Nanotech) held at 120° C. The water dosing was conducted by utilizing the following ALD sequence (time in s): t1-t2-t3, where t1 is the water pulse time, t2 is the exposure time (i.e., the time without pumping), and t3 is the pumping time. The water source was kept at room temperature, and the deposition was conducted by utilizing 100 cycles of 0.015-120-120 sequences. The nitrogen flow rate in the ALD chamber was 5 sccm during the whole process. The sample obtained after this process was designated "Sn-SIM (1 cycle)." Thereafter, NU-1000 was replaced by 80 mg of Sn-SIM (1 cycle) and all the experimental steps mentioned above were conducted again, resulting in the sample designated "Sn-SIM (2 cycle)." The whole process was conducted again starting with 80 mg of Sn-SIM (2 cycle) to synthesize the sample designated "Sn-SIM (3 cycle)," and again starting with 80 mg of Sn-SIM (3 cycle) to make "Sn-SIM (4 cycle)."

Preparation of electrodes. IDEs with 180 pairs of platinum fingers and a 5-μm gap (MicruX Technologies, ED-IDE3-Pt) were used for all current-voltage (I-V) and gas sensing measurements. NU-1000 and all the Sn-SIM materials were first dispersed in acetone to make suspensions by sonication, with a concentration of 10 mg/mL. Thereafter, NU-1000/IDE, Sn-SIM (1 cycle)/IDE, Sn-SIM (2 cycle)/IDE, Sn-SIM (3 cycle)/IDE, and Sn-SIM (4 cycle)/IDE were prepared by successively drop-casting 2 μL of corresponding suspensions on bare IDEs until full coverage was achieved. For conductivity measurements, 2 μL of diluted suspensions (0.1 mg/mL) were drop-casted once on bare IDEs to deposit bridging crystals between the gaps of IDEs. All the obtained electrodes were dried at room temperature before any measurement.

Instrumentation. Powder XRD (PXRD) patterns were collected on a Rigaku ATX-G workstation. Nitrogen adsorption isotherms were collected on an ASAP 2020 (Micromeritics). Inductively coupled plasma optical emission spectroscopy (ICP-OES) measurements were conducted on a Thermo iCAP 7600 and utilized to obtain the Sn loadings of all samples; the procedure for digesting MOF samples for ICP-OES measurements has been reported previously. (See, e.g., Mondloch et al., 2013) X-ray photoelectron spectroscopy (XPS) was measured on ESCALAB 250Xi, Thermo Scientific. SEM and EDS measurements were conducted on a Hitachi SU8030. Thermogravimetric analysis (TGA) was performed using a TA Instruments Q500 under air flow at a ramp rate of 10° C./min from 25 to 600° C.

Synchrotron PXRD data suitable for DED analysis were collected at beamline 17-BM at the Advanced Photon Source using 17.0 keV (0.45220 Å). (See, e.g., Yakovenko, A. A. et al., *J. Appl. Crystallogr.* 2013, 46 (2), 346-353.) Data were collected using an amorphous silicon-based area detector. Geometric corrections and reduction to one-dimensional data used GSAS-II. (See, e.g., Toby, B. H., et al., *J. Appl. Crystallogr.* 2013, 46 (2), 544-549.) Lattice parameters and peak intensities were extracted from diffraction patterns via Le Bail whole-pattern fitting using Jana2006 based on the reported structural model for NU-1000 (csq topology, P6/mmm, a~40 Å, c~17 Å). (See, e.g., Mondloch et al., 2013; Le Bail, A., *J. Non-Cryst. Solids* 1995, 183 (1), 39-42; and Petricek, V., et al., *Zeitschriftfur Kristallographie—Crystalline Materials,* 2014; Vol. 229, p 345.) Lattice and pseudo-Voigt profile parameters were refined over a 0.5-10° 2θ range. Structure envelopes were generated using the intensities of low-index reflections. DED maps were then obtained via subtraction of the envelope for pristine NU-1000 from the envelope for Sn-SIM materials.

IV curves of the IDEs deposited with NU-1000 and Sn-SIM materials were measured on a CHI 660 potentiostat (CH Instruments, Inc., USA), with a two-electrode setup connected to a drop-cell connector (MicruX Technologies, ED-DROP-CELL) with the IDE. All IV curves were measured in air at room temperature. Gas sensing experiments were conducted in a sealed glass cell installed with one gas inlet, one gas outlet, and two copper wires which connected the IDE inside the cell to a portable potentiostat (CHI 1200, CH Instruments, Inc., USA). 5% hydrogen in nitrogen or air continuously flowed into the cell through the gas inlet. A constant voltage of 1 V was applied to the IDE during all gas sensing experiments.

Estimation of volumetric surface area. The volume of the unit cell in NU-1000 is 22145.3 Å$^3$ according to the crystal structure, including three hexa-zirconium nodes and six TBAPy linkers. The molecular weight of the atoms presented in each unit cell was calculated by considering the atoms presented in NU-1000 and the installed Sn atoms, as the number of Sn on each node had been obtained by ICP-OES. Two new oxo ligands were considered with each Sn atom. Thereafter, according to the molecular weight and the volume of unit cell, the densities of NU-1000, Sn-SIM (1 cycle), Sn-SIM (2 cycle), and Sn-SIM (3 cycle) were estimated to be 0.49, 0.63, 0.80, and 0.96 g/cm$^3$, respectively. The galvanometric BET surface areas of these materials can then be converted into volumetric BET surface areas by multiplying their densities.

Estimation of conductivity. For conductivity measurements, a dilute suspension (0.1 mg/mL) of each sample was coated on a bare IDE, and the I-V curve of each coated IDE was measured in air after drying. The number of bridging crystals between the gaps of each IDE was estimated via SEM after the I-V measurements. The approach for measuring electrical conductivity by bridging microcrystals between the five-micrometer gaps prevented the estimation of conductivity contributed from the tin oxide installed in the NU-901-like second phase in the middle (about 20%) of those crystals. The electrical conductivity (a) of each sample was then estimated by the following equation, $$\sigma = \frac{Gl}{nA}$$

where G is the electrical conductance estimated from the slope within the linear region of the I-V curve between +0.5 V and −0.5 V, l is the gap width of the IDE, which is 5 µm, n is the number of bridging crystals between the gaps of the full IDE, and A is the average cross-section area of single MOF crystal, which is 5.7 µm$^2$ estimated by assuming that the cross section of the crystal is a regular hexagon with an average maximal diameter of 2.96 µm.

Results and Discussion

Figure 1A:
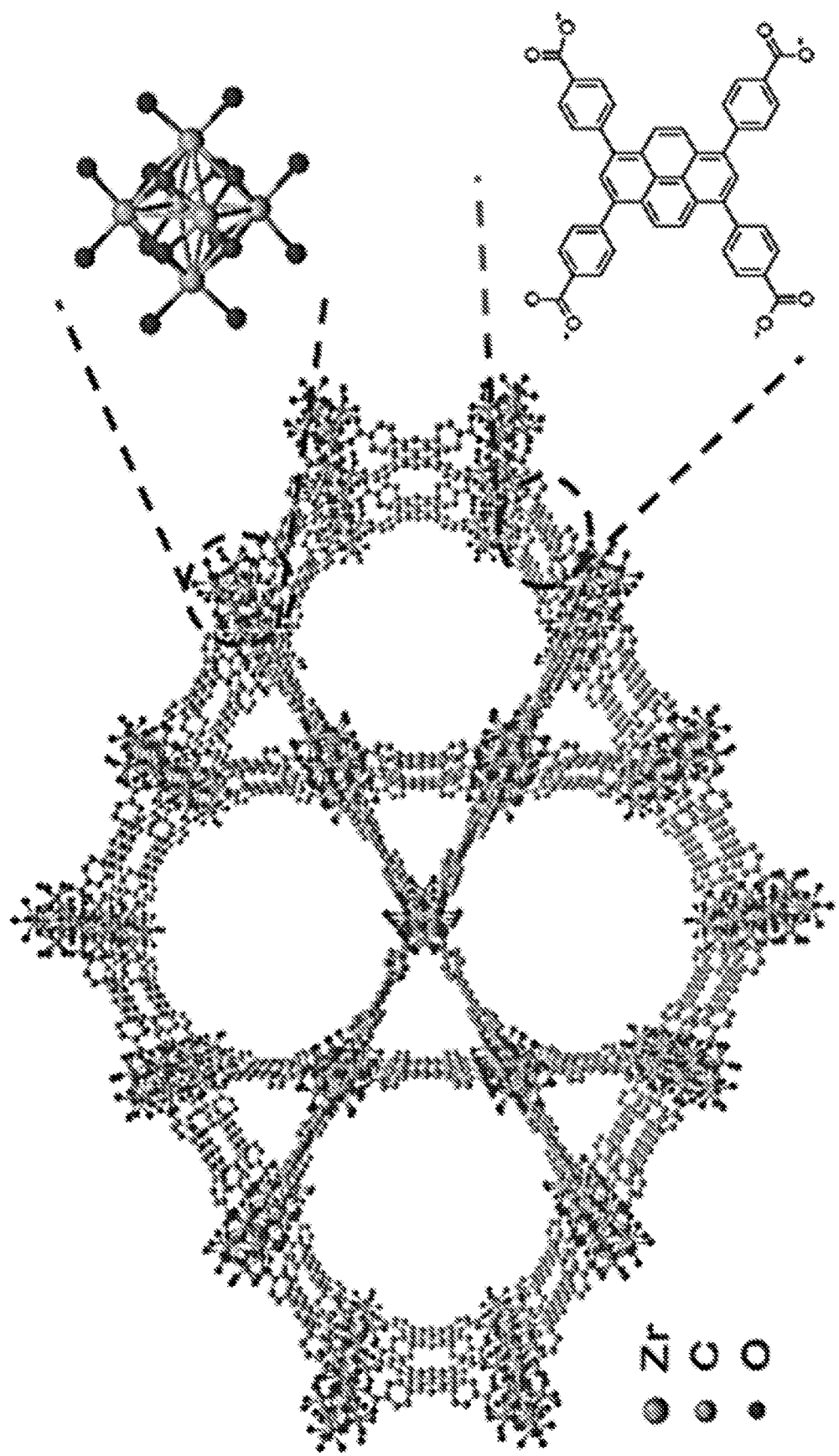
FIG. 1A shows a top view of the crystal structure of NU-1000. For simplicity, hydrogen atoms are not shown.

FIG. 1A illustrates the structure of NU-1000. Constructed with tetra-phenylcarboxylate-pyrene units as linkers, the material presents one-dimensional hexagonal mesopores and triangular micropores, with ca. 8 Å windows connecting the two. Thus, the MOF is readily permeated by small and medium-sized molecules, including reactive inorganic and organometallic complexes. Here, the water and hydroxyl reactivity of (Sn(amd)$_2$) was capitalized upon to graft the complex onto the MOF nodes. When delivered via a heptane solution, it was found that 4.3 tin atoms, on average, were grafted per node—presumably with retention of one anionic amd$^{1-}$ ligand per tin ion. (The residual amd$^{1-}$ ligand presumably serves to prevent reaction of additional Sn(amd)$_2$ complexes with the initially grafted tin ions; i.e., it serves to self-limit the grafting reaction.) In a second step, the functionalized material was dosed with steam at 120° C. in the reaction chamber of an ALD tool. Treatment with steam is designed to remove remaining precursor ligands (here as volatile amdH), replace them with oxy ligands (aqua, hydroxy, and/or oxo ligands), and to make the installed ions receptive to self-limiting, secondary grafting of additional tin ions. Indeed, it was found that after two Sn-SIM cycles (tin precursor complex, followed by steam), the loading increased to 9 tin ions per node. After three Sn-SIM cycles, the measured loading (ICP-OES) was 14 tin ions, and after four it was ~24.

Figure 2:
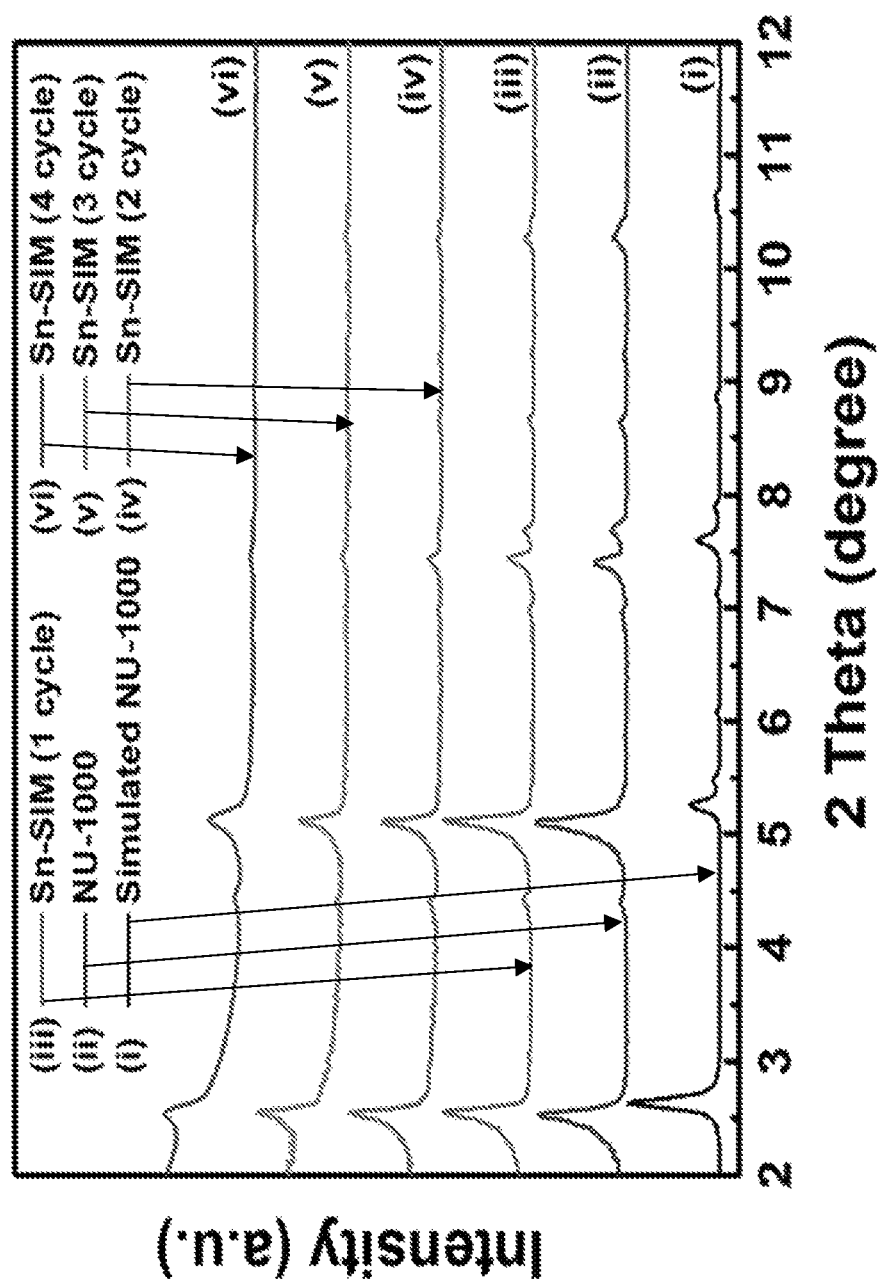
FIG. 2 shows X-ray diffraction (XRD) data of NU-1000, Sn-SIM (1 cycle), Sn-SIM (2 cycle), Sn-SIM (3 cycle), Sn-SIM (4 cycle), and the simulated data of NU-1000.
Figure 3B:
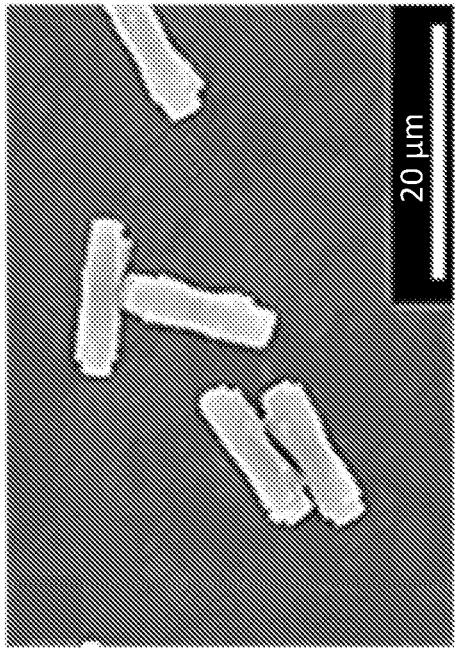
FIG. 3B shows an SEM image of Sn-SIM (3 cycle).
Figure 3D:
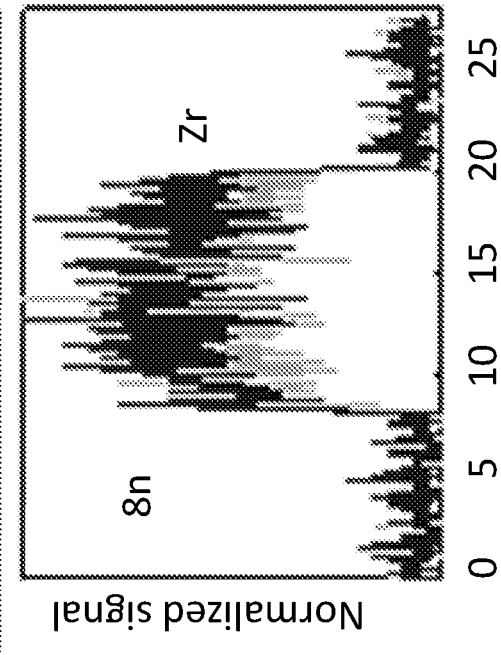
FIG. 3D shows distributions of Zr and Sn obtained by energy-dispersive X-ray spectroscopy (EDS) from the line shown in FIG. 3C.
Figure 3A:
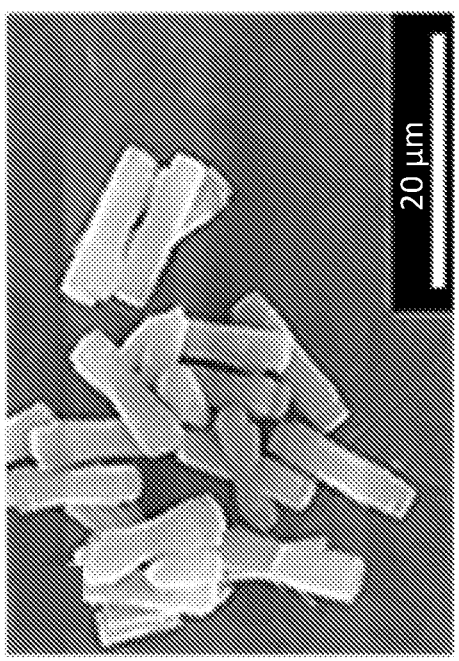
FIG. 3A is a scanning electron microscopy (SEM) image of NU-1000.
Figure 3C:
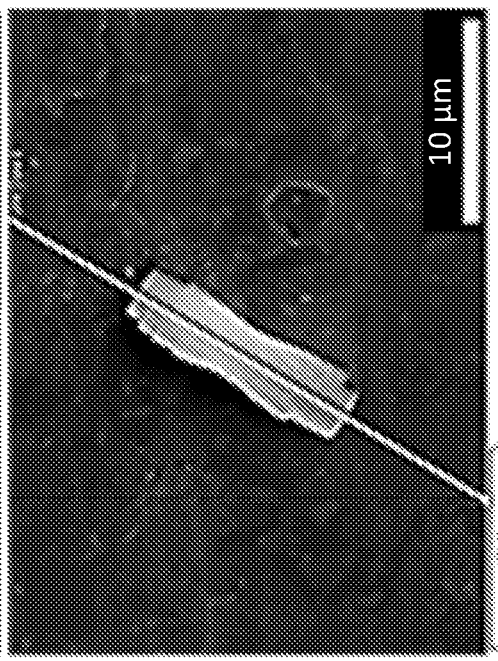
FIG. 3C is an SEM image of one crystal in Sn-SIM (3 cycle).

PXRD measurements (FIG. 2) reveal that the crystallinity of NU-1000 is preserved after multiple Sn-SIM cycles and, together with other measurements, underscore the ability of the Zr-MOF to withstand repetitive, high-temperature exposure to water. SEM images (FIG. 3) show that the MOF samples exist as hexagonal rod-shaped microcrystals and that their size and morphology are unaffected by repetitive Sn-SIM treatment. Elemental (Zr and Sn) line-scan measurements based on EDS (FIGS. 3C and 3D) established that for 1, 2, or 3 synthesis cycles, the SIM method installs tin ions uniformly in the MOF. XPS measurements establish that the installed tin ions are present in oxidation state IV rather than the oxidation state of tin in the precursor molecule, i.e., II. As the water reservoir used for steam dosing was equilibrated with air, it can be inferred that O$_2$ is responsible for the conversion from Sn(II) to Sn(IV). Thermogravimetric analysis reveals that the residual mass fractions of zirconium oxide and/or tin oxide in NU-1000, Sn-SIM (1 cycle), Sn-SIM (2 cycle), and Sn-SIM (3 cycle) after calcining in air are 29.0%, 38.6%, 46.7%, and 52.0%, respectively.

Figure 1B:
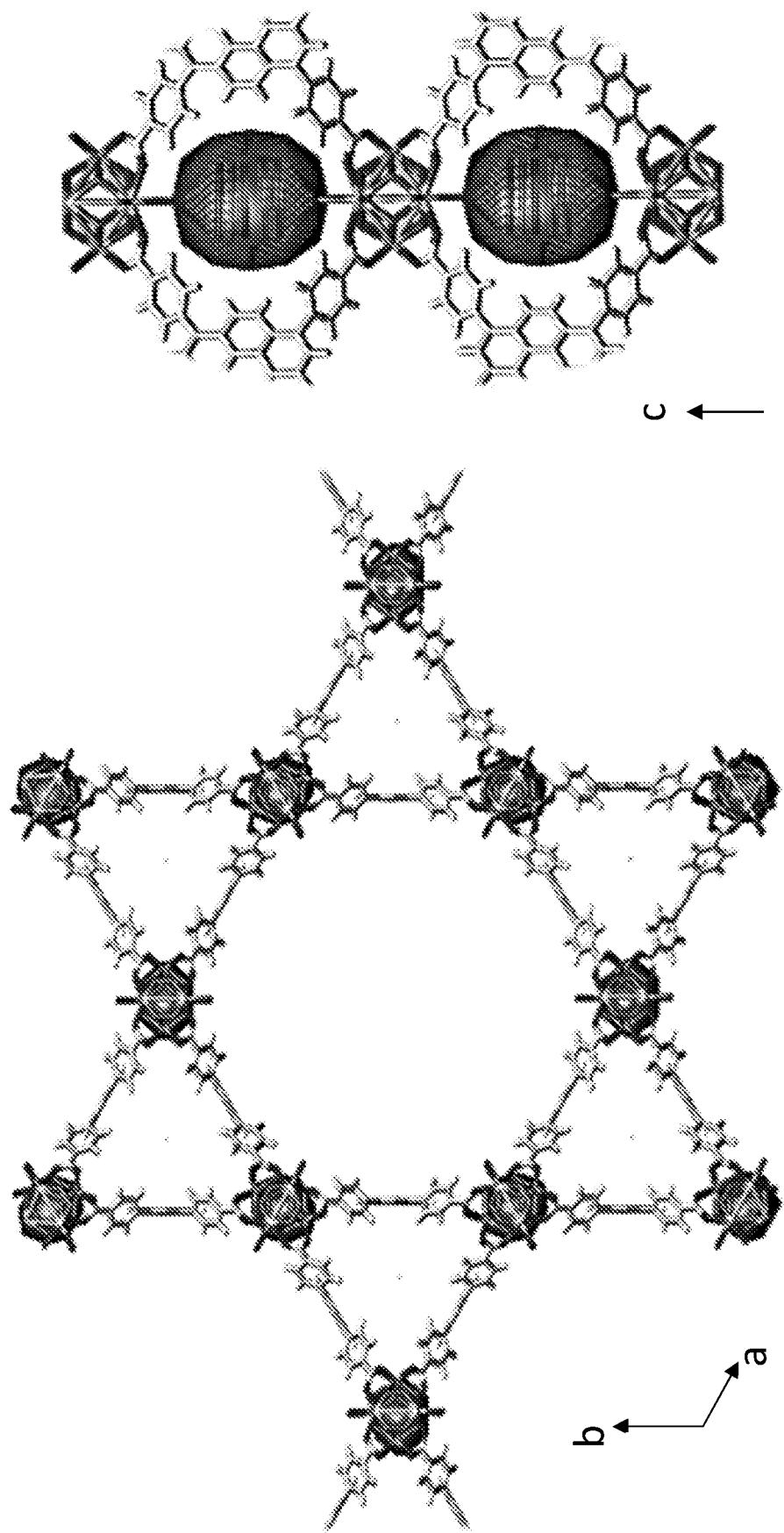
FIG. 1B is a difference electron density (DED) map of Sn-solvothermal installation in MOFs (SIM) (1 cycle).

The persistence of MOF crystallinity makes possible the collection of high resolution (synchrotron derived) PXRD data for various Sn-SIM NU-1000 samples. Subsequent DED analysis can provide information about the siting of SIM-installed tin ions. Briefly, however, DED maps were obtained by subtracting the X-ray derived structure envelope for pristine NU-1000 from that for a tin-modified version. FIG. 1B shows that after a single SIM cycle (both Sn(amd)$_2$ and steam), tin ions are sited between nodes, along the MOF's c crystallographic axis. Thus, the installed metal ions are present as tetra-tin(IV)oxy clusters, with grafting of each cluster to a pair of hexa-zirconium(IV)oxy nodes. The siting leaves tin-oxide clusters separated by electrically insulating nodes. (For simplicity, the SIM-synthesized clusters will be referred to as tin-oxide, while it is recognized that the tin(IV) species no doubt ligate hydroxide (and possibly also water) in addition to O$^{2-}$.)

Figure 1C:
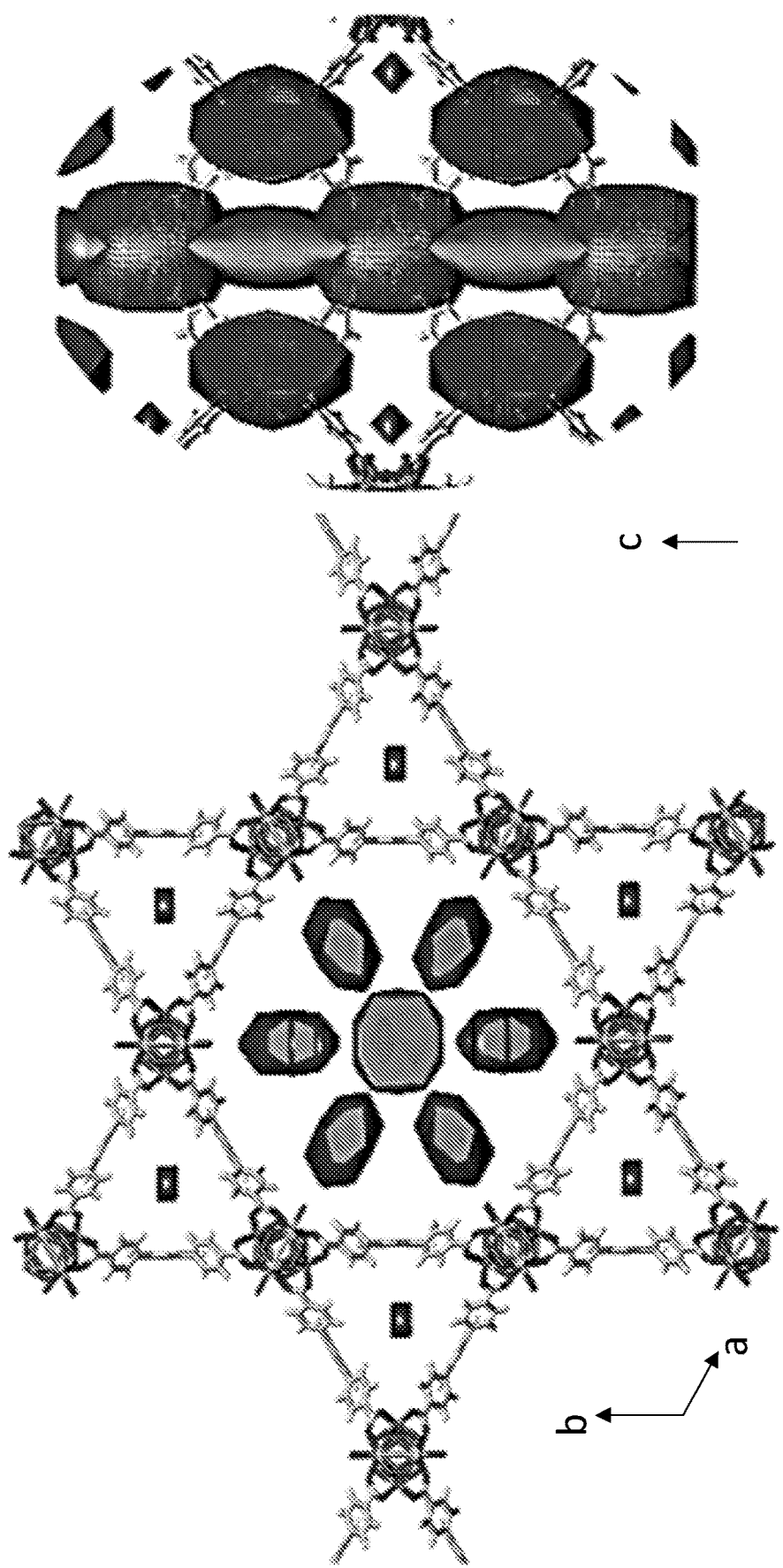
FIG. 1C is a DED map of Sn-SIM (3 cycle). The electron density of tin oxide is presented in dark grey.

DED mapping with extra electron density from tin oxide was obtained with Sn-SIM (3 cycle), as shown in FIG. 1C. After three cycles of SIM, the initially formed clusters were interconnected along the c-axis and constituted extended tin-oxide structures located at the vertices of the 1D pores. It is worth noting that, after three Sn-SIM cycles, the DED map also shows added electron density in the center of the hexagonal pore. As prepared here, NU-1000 samples contain a second phase of uncertain structure, but possibly similar to that of NU-901 which features 1D diamond-shaped channels. (See, e.g., Kung, C.-W., et al., Chem. Mater. 2013, 25 (24), 5012-5017.) It has been previously reported that if the single-crystal X-ray data are fit to a single structure, the centers of the hexagonal channels appear to contain an additional node, but with an occupancy of only about 20%. (Mondloch et al., 2013) The "extra" electron density revealed in the Sn-SIM (3 cycle) DED map is likely due to the presence of a second phase, also suitable for tin grafting, and subsequent neglect of that phase in the analysis.

Figure 4A:
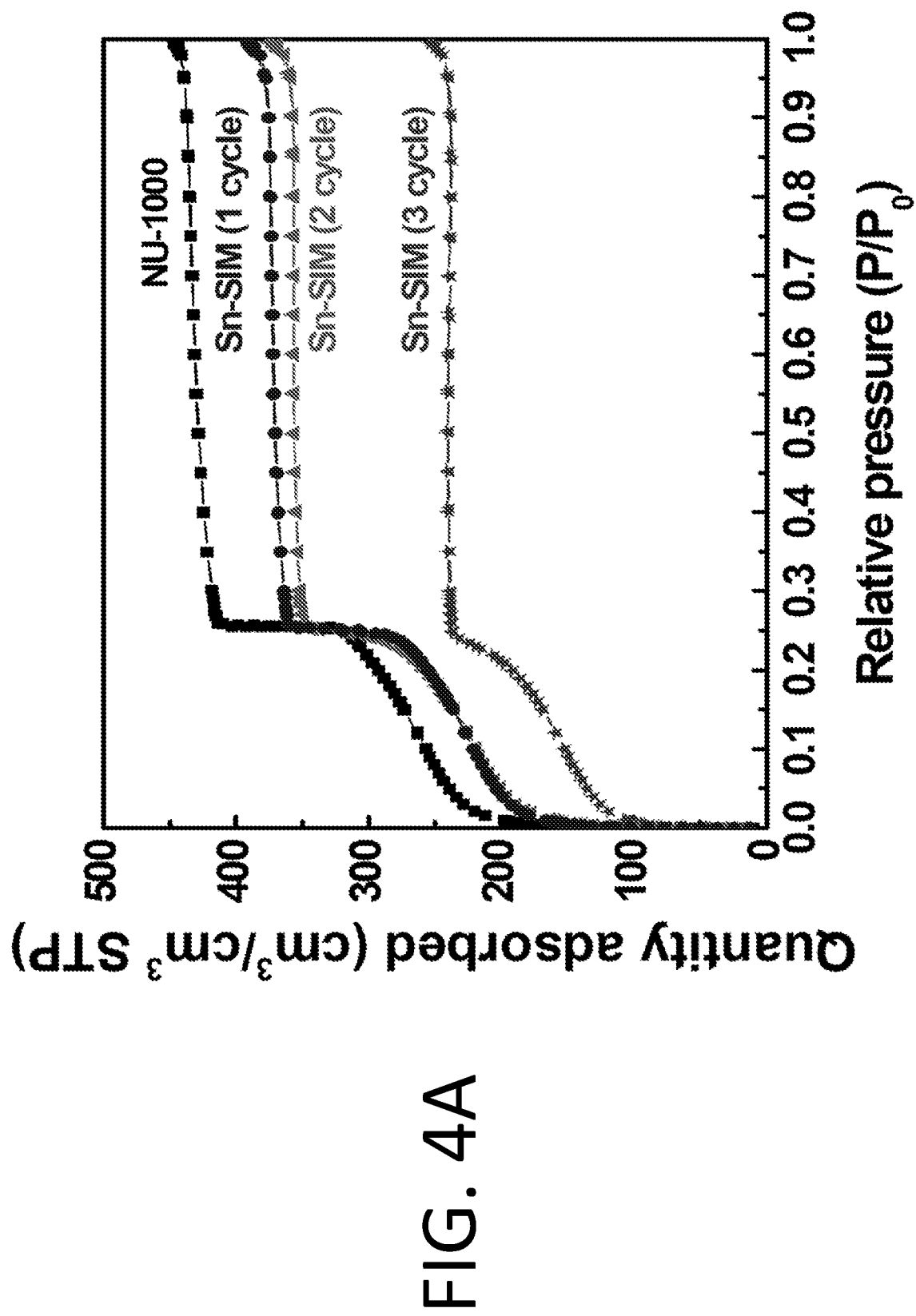
FIG. 4A depicts nitrogen adsorption-desorption isotherms of NU-1000, Sn-SIM (1 cycle), Sn-SIM (2 cycle), and Sn-SIM (3 cycle).
Figure 4B:
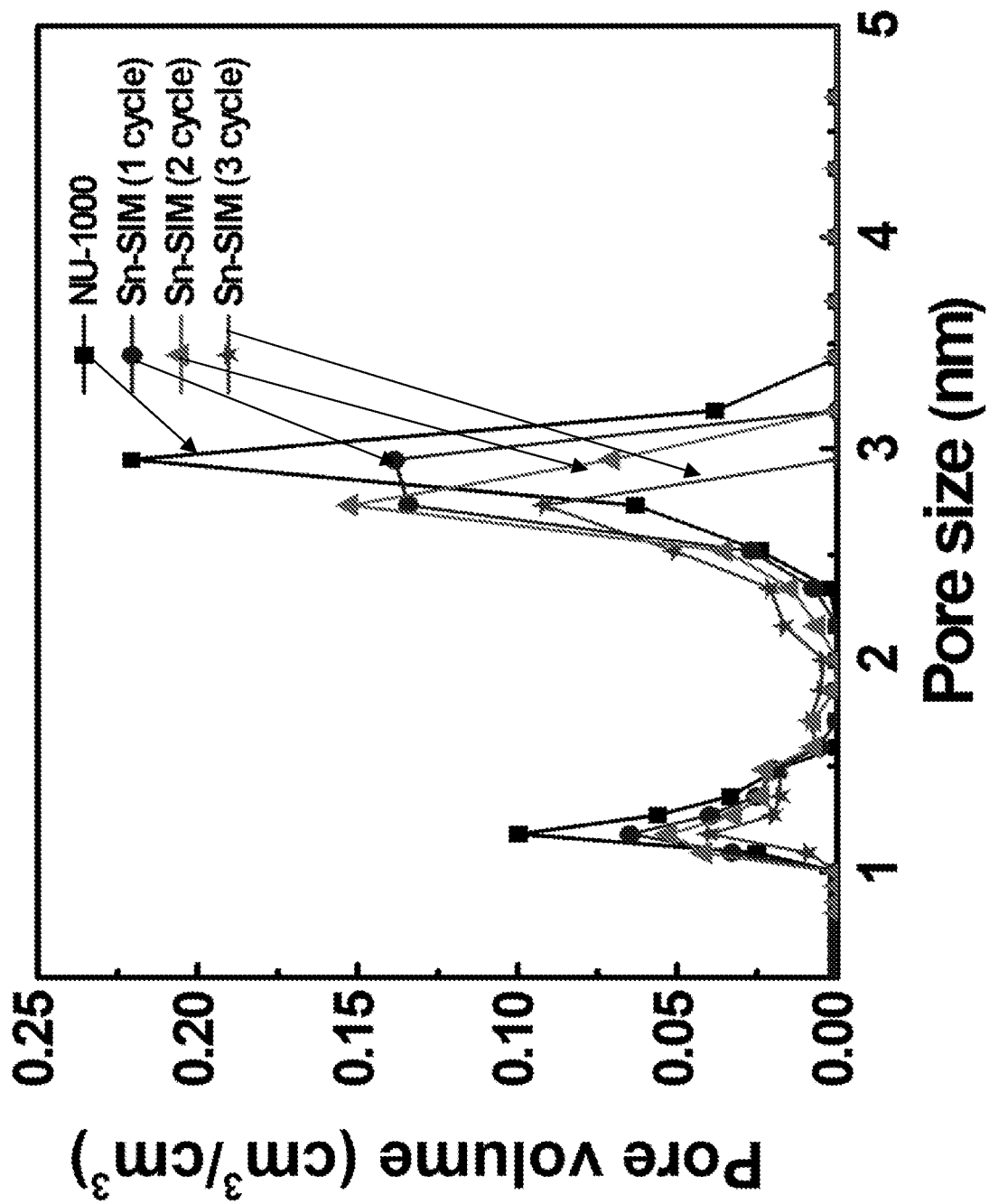
FIG. 4B shows density functional theory (DFT) pore size distributions of NU-1000, Sn-SIM (1 cycle), Sn-SIM (2 cycle), and Sn-SIM (3 cycle).

To gauge the porosity of the MOF following tin-oxide installation of tin, N$_2$ adsorption-desorption experiments were conducted at 77K; the gravimetric isotherms of NU-1000, Sn-SIM (1 cycle), Sn-SIM (2 cycle), and Sn-SIM (3 cycle) were obtained. The corresponding volumetric isotherms are shown in FIG. 4A, where the volumetric presentation avoids the pitfalls of isotherm comparisons for versions of samples having differing unit-cell masses. Both sets of isotherms indicate retention of mesoporosity following tin-oxide introduction, as evidenced by the step at relative pressures of about 0.25 and as summarized by the pore-size distribution (PSD) plots in FIG. 4B. Consistent with DED mapping, the PSD plots indicate only slight shrinkage of the hexagonal pore widths (from ~31 Å to no less than ~27 Å) following tin-oxide installation at the channel vertices. Similarly, consistent with DED mapping, no change in the width of triangular pores was evident.

The nitrogen isotherms returned BET surface areas of 2100, 1410, 1130, and 680 $m^2/g$, for NU-1000, Sn-SIM (1 cycle), Sn-SIM (2 cycle), and Sn-SIM (3 cycle), respectively. The significant decrease in gravimetric surface area can be attributed, in part, to the aforementioned mass gain due to tin incorporation; the unit-cell mass of Sn-SIM (3 cycle) is about double of that of NU-1000 due to the presence of 14 tin ions (and charge-balancing oxy ligands) for each $Zr_6$ node. Volumetric parameters, therefore, may be more instructive than gravimetric parameters. (For simplicity, and in the absence of more detailed information, the samples were treated as if each tin ion was accompanied by two new oxo ligands.) The volumetric BET surface areas were 1020, 890, 900, and 650 $m^2/cm^3$, for NU-1000, Sn-SIM (1 cycle), Sn-SIM (2 cycle), and Sn-SIM (3 cycle), respectively. In other words, roughly two-thirds of the initial surface area, and slightly more than half the total initial pore volume (FIG. 4A), remained after three Sn-SIM cycles.

To investigate electrical conductivity of NU-1000 and the modified MOFs, MOF suspensions were drop-casted on IDEs featuring electrode spacings of 5 μm, which can be spanned by the microcrystals of ~10 μm in length. The drop-casted MOF suspensions were then allowed to dry in air at room temperature. FIG. 5A shows room temperature measured I-V curves for NU-1000/IDE, Sn-SIM (1 cycle)/IDE, Sn-SIM (2 cycle)/IDE, and Sn-SIM (3 cycle)/IDE. No measurable current was observed for NU-1000/IDE and Sn-SIM (1 cycle)/IDE, indicating that both materials are electrically insulating. In contrast, measurable currents were observed for Sn-SIM (2 cycle) and Sn-SIM (3 cycle). The slope of the I-V curve for Sn-SIM (3 cycle)/IDE at 0 V is about five times higher than that for Sn-SIM (2 cycle)/IDE. Inclusion of a fourth Sn-SIM cycle yielded no further increase in slope—consistent with the EDS-based finding that the fourth installation does not span the length of the microcrystals and, thus, should not contribute to the measured conductance.

The combined results indicate that the presence of tin-oxide and continuous c-axis strands of the added oxide resulted in the conductivity; see FIG. 1 and accompanying discussion of DED mapping and tin-oxide siting. To obtain estimates of the electrical conductivity values, diluted suspensions of NU-1000, Sn-SIM (1 cycle), Sn-SIM (2 cycle), and Sn-SIM (3 cycle) were drop-casted on IDEs to deposit bridging crystals across the gaps of IDEs, and the number of bridging crystals on each IDE was estimated via SEM. FIG. 5B shows the obtained electrical conductivities NU-1000, Sn-SIM (1 cycle), Sn-SIM (2 cycle), and Sn-SIM (3 cycle), along with their volumetric BET surface areas. The conductivity of Sn-SIM (3 cycle) is $1.8 \times 10^{-7}$ S/cm, placing the conductive-glass-modified, and still mesoporous, MOF material in the semiconducting regime (at least phenomenologically).

It was reasoned that the conductivity of Sn-SIM would be susceptible to modulation by hydrogen and that Sn-SIM/IDE assemblies could function as $H_2$ sensors. FIG. 6 shows that the conductance of Sn-SIM (3 cycle)/IDE substantially increased in the presence of flowing hydrogen (5% in $N_2$) and then decreased when the atmosphere was switched to flowing air—with reversible changes of about 1,000-fold (ignoring spikes). The response times to 5% hydrogen and air were about 400 s and 5-10 s, respectively. By assuming a linear relationship between the change in conductance and the concentration of hydrogen, the limit of detection of the Sn-SIM (3 cycle)/IDE-based sensor was about 0.02% hydrogen based on the signal-to-noise ratio of 3. Consistent with the role of tin-oxide as the active element, essentially no conductance (and no change in conductance) was observed when NU-1000/IDE was subjected to the same gas exposure and switching protocol; see FIG. 6. A much longer response time was observed with the Sn-SIM (3 cycle)/IDE when nitrogen flow was used to replace the air flow during the switching process, which indicates that the oxidation of tin oxide via oxygen was involved during the switching process shown in FIG. 6. These preliminary findings with Sn-SIM indicate that this approach to engendering MOF conductivity can be more generally useful for gas or vapor sensing, especially when other SIM compositions are used.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A metal-organic framework material comprising:
   a porous metal-organic framework comprising zirconium nodes connected by organic linkers comprising 1,3,6,8-tetrakis(p-benzoic acid)pyrene units, wherein the zirconium nodes are capped by hydroxyl ligands; and
   a plurality of continuous strands comprising a metal oxide running through the metal-organic framework, wherein the continuous strands of the metal oxide are grafted to oxygen atoms on the zirconium nodes, the metal oxide of the continuous strands is a tin oxide, and
   the metal-organic framework material is porous.

2. The material of claim 1, wherein the continuous strands and the metal-organic framework material are electrically conductive.

3. The material of claim 1, wherein the metal nodes comprise an octahedral $Zr_6$ cluster having twelve octahedral edges and eight of the twelve octahedral edges of the metal nodes are connected to the 1,3,6,8-tetrakis(p-benzoic acid)pyrene units.

4. The material of claim 1, wherein the metal-organic framework has a tin loading of at least 14 tin (IV) ions per $Zr_6$ node.

5. The material of claim 3, wherein the material has a conductivity of at least $1 \times 10^{-7}$ S/cm.

6. The material of claim 1, wherein the continuous strands have widths of 1 nm or less.

7. A method of detecting hydrogen using a metal-organic framework material comprising:
- a porous metal-organic framework, the metal-organic framework comprising zirconium nodes connected by organic linkers comprising 1,3,6,8-tetrakis(p-benzoic acid)pyrene units, wherein the zirconium nodes are capped by hydroxyl ligands; and
- a plurality of continuous strands of an electrically conductive metal oxide running through the metal-organic framework, wherein the continuous strands of the electrically conducive metal oxide are grafted to oxygen atoms on the zirconium nodes, the metal oxide of the continuous strands is a tin oxide, and
- the metal-organic framework material is porous and electrically conductive,
- the method comprising:
- exposing the metal-organic framework material to an environment comprising hydrogen; and
- measuring an increase in the conductance of the metal-organic framework material.

8. The metal-organic framework material of claim 1, wherein the metal-organic framework is NU-1000.

\* \* \* \* \*